US010226229B2

(12) United States Patent
Hongou et al.

(10) Patent No.: US 10,226,229 B2
(45) Date of Patent: Mar. 12, 2019

(54) ULTRASOUND DIAGNOSIS APPARATUS

(75) Inventors: Hironobu Hongou, Otwara (JP); Yasuo Miyajima, Utsunomiya (JP); Nobuyuki Iwama, Nasushiobara (JP); Isao Uchiumi, Nasushiobara (JP); Masaaki Ishitsuka, Nasushiobara (JP); Toru Hirano, Otawara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 431 days.

(21) Appl. No.: 13/981,507

(22) PCT Filed: Aug. 10, 2012

(86) PCT No.: PCT/JP2012/070572
§ 371 (c)(1),
(2), (4) Date: Jul. 24, 2013

(87) PCT Pub. No.: WO2013/024832
PCT Pub. Date: Feb. 21, 2013

(65) Prior Publication Data
US 2013/0310695 A1    Nov. 21, 2013

(30) Foreign Application Priority Data

Aug. 18, 2011 (JP) .................. 2011-178935

(51) Int. Cl.
*A61B 8/00* (2006.01)
*G01S 7/52* (2006.01)
(Continued)

(52) U.S. Cl.
CPC .............. *A61B 8/4483* (2013.01); *A61B 8/44* (2013.01); *A61B 8/54* (2013.01); *G01S 7/5208* (2013.01);
(Continued)

(58) Field of Classification Search
CPC ...... A61B 8/00; A61B 8/13–8/15; A61B 8/44; A61B 8/4483; A61B 8/54; G10K 11/346;
(Continued)

(56) References Cited

U.S. PATENT DOCUMENTS

| 5,675,554 A | 10/1997 | Cole et al. |
| 5,856,955 A | 1/1999 | Cole et al. |

(Continued)

FOREIGN PATENT DOCUMENTS

| JP | 57 37441 | 3/1982 |
| JP | 1 164354 | 6/1989 |

(Continued)

OTHER PUBLICATIONS

International Search Report dated Nov. 13, 2012 in PCT/JP12/070572 Filed Aug. 10, 2012.

*Primary Examiner* — Peter Luong
(74) *Attorney, Agent, or Firm* — Oblon, McClelland, Maier & Neustadt, L.L.P.

(57) ABSTRACT

To provide an ultrasound diagnosis apparatus capable of appropriately assigning a transmission delay time of a group to a transducer without complicated wires. The ultrasound diagnosis apparatus of the embodiment comprises a plurality of transducers, a timing pulse generator, a switch part, and a switch controller. Ultrasound waves are transmitted to the transducers. The timing pulse generator has output terminals for outputting timing pulses based on a delay time to a channel corresponding to each of the transducers, in which a plurality of output terminals are divided into groups and each group has the output terminals of a specific number greater than two. The timing pulse generator then generates the transmission delay time within a predetermined time range for the each group. The switch part selectively connects the channels with the output terminals. The switch controller divides the plurality of channels into channel regions of the same number as the specific number, and controls the switch part so as to correspond between the groups and the regions by connecting the channels and the output terminals.

3 Claims, 10 Drawing Sheets

(51) Int. Cl.
*G10K 11/34* (2006.01)
*G01S 15/89* (2006.01)

(52) U.S. Cl.
CPC ...... *G01S 7/52085* (2013.01); *G01S 15/8927* (2013.01); *G10K 11/346* (2013.01); *G01S 15/8993* (2013.01)

(58) Field of Classification Search
CPC ............... G01S 7/5208; G01S 7/52085; G01S 15/8927; G01S 15/8993
See application file for complete search history.

(56) References Cited

U.S. PATENT DOCUMENTS

| | | | |
|---|---|---|---|
| 5,995,450 A | 11/1999 | Cole et al. | |
| 6,104,673 A | 8/2000 | Cole et al. | |
| 6,126,602 A | 10/2000 | Savord et al. | |
| 6,172,939 B1 | 1/2001 | Cole et al. | |
| 6,363,033 B1 | 3/2002 | Cole et al. | |
| 7,217,243 B2 | 5/2007 | Takeuchi | |
| 2005/0096545 A1 | 5/2005 | Haider et al. | |
| 2007/0232924 A1* | 10/2007 | Karasawa | A61B 8/14 600/459 |
| 2010/0010350 A1 | 1/2010 | Baba et al. | |
| 2011/0021921 A1 | 1/2011 | Tsao | |

FOREIGN PATENT DOCUMENTS

| | | |
|---|---|---|
| JP | 3 267052 | 11/1991 |
| JP | 10 507936 | 8/1998 |
| JP | 2005 34634 | 2/2005 |
| JP | 2005 131409 | 5/2005 |
| JP | 2007 44193 | 2/2007 |
| JP | 2008 55087 | 3/2008 |
| JP | 2010 42244 | 2/2010 |
| JP | 2011 19858 | 2/2011 |

* cited by examiner

FIG. 2

|     |     |     |     |     |     |     |     |
|-----|-----|-----|-----|-----|-----|-----|-----|
| a11 | a12 | a13 | a14 | a15 | a16 | a17 | a18 |
| a21 | a22 | a23 | a24 | a25 | a26 | a27 | a28 |
| a31 | a32 | a33 | a34 | a35 | a36 | a37 | a38 |
| a41 | a42 | a43 | a44 | a45 | a46 | a47 | a48 |
| a51 | a52 | a53 | a54 | a55 | a56 | a57 | a58 |
| a61 | a62 | a63 | a64 | a65 | a66 | a67 | a68 |
| a71 | a72 | a73 | a74 | a75 | a76 | a77 | a78 |
| a81 | a82 | a83 | a84 | a85 | a86 | a87 | a88 |
| a91 | a92 | a93 | a94 | a95 | a96 | a97 | a98 |

A0 indicates the 3×3 block in the upper-left (a11–a33).

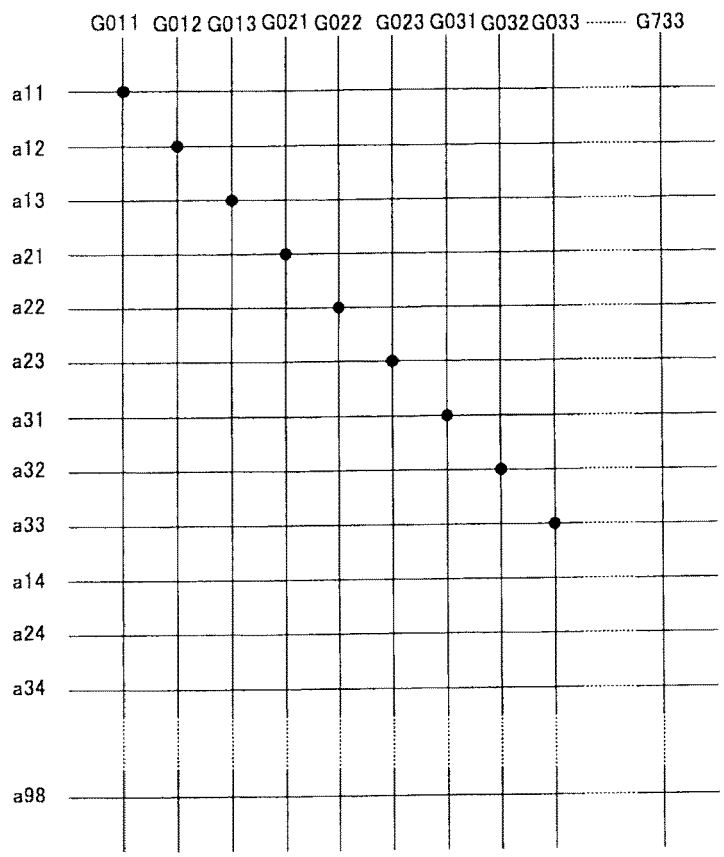

ULTRASOUND DIAGNOSIS APPARATUS

TECHNICAL FIELD

The embodiment of the present invention relates to an ultrasound diagnosis apparatus.

BACKGROUND ART

Recently, a 2D array probe capable of displaying real time 3-dimensional ultrasound images has been developed for use with making diagnoses. This probe has an electronic circuit that controls transmission and reception via several thousand transducers.

Upon transmission, a delay time is set such that ultrasound wavefronts transmitted from the transducers are justified on a focal point, timing pulses based on the delay time are generated from a delay circuit of a timing pulse generator, and the timing pulses are output from output terminals to channels (signal paths to or from the transducer) of the transducers.

Subsequently, a high-frequency voltage pulse based on the timing pulse is output from the pulser to the transducer, thereby activating the transducer.

The timing pulse generator includes an ASIC (Application Specific Integrated Circuit) that unifies circuits having a plurality of functions including a delay circuit.

The timing pulse generator is housed in the case of the probe. Normally, the capacity of the case is about 100 cc only, necessitating that the circuit size of the timing pulse generator be preferably made as small as possible.

If the delay circuit is composed of a single circuit, the circuit size becomes larger. Therefore, as illustrated in FIG. 8, the delay circuit is composed of two common circuits, namely, a rough adjustment circuit for setting a rough delay time and a fine adjustment circuit for setting a more specific delay time than the rough delay time. Further, two kinds of circuits are provided for each group by dividing the arrayed transducer into a plurality of regions and dividing the timing pulse generator into a plurality of groups. Further, the groups are allowed to correspond to the regions (the region composed of a plurality of transducers.) In FIG. 8, some groups among the plurality of groups are illustrated by the codes G0 to G7. For example, the group G0 has a rough adjustment circuit for setting a delay time of 0 [μs] and a fine adjustment circuit for setting nine delay times at intervals of 0.1 [μs]. In other words, in the group G0, within a time range of 0 [μs] to 0.8 [μs], a delay time is assigned to the transducer within the region corresponding to the group G0. In addition, for example, the group G7 has a rough adjustment circuit for setting a delay time of 7.0 [μs] and a fine adjustment circuit for setting nine delay times at intervals of 0.1 [μs]. In other words, in the group G7, within a time range of 7.0 [μs] to 7.8 [μs], a delay time is assigned to the transducer within the region corresponding to the group G7. As described above, it is possible to make the delay time range different for each group. Thus, the delay time may be assigned to the transducer within the region by using two kinds of circuits in the group, thereby making each circuit compact and reducing the entire circuit size. Further, as the transducer corresponds to the channel, the region of the transducer may be sometimes referred to as the channel region.

The group of the timing pulse generator is selected, for example, in accordance with a diagnosis mode. In this case, the region corresponding to this group is unambiguously selected.

PRIOR ART DOCUMENT

Patent Document

[Patent Document 1] Japanese Unexamined Patent Application Publication No. 2010-42244

SUMMARY OF THE INVENTION

Problems to be Solved by the Invention

However, depending on the unambiguously selected region, the transducers in the region are separately placed beyond an acceptable range, with the delay times of such transducers occasionally exceeding the set range. As a result, the delay of the transducers becomes insufficient and the deflection angle and aperture are limited, leading to deterioration of the image quality and sensitivity.

FIG. 9 is a pattern diagram partially illustrating an ultrasound probe according to a comparative example. FIG. 9 illustrates the transducers arranged as a 9×8 matrix provided using matrix numbers (a11 to a98), with the regions corresponding to groups G1 and G2 represented as regions A1 and A2 encircled by bold lines.

How to assign the delay time to the transducer will be explained with reference to FIG. 9. The range of the delay time of the group G1 to be assigned to the region A1 is determined as 0 [μs] to 0.8 [μs]. In addition, the range of the delay time of the group G2 to be assigned to the region A2 is determined as 0.3 [μs] to 1.1 [μs].

In the region A1 illustrated in FIG. 9, the delay times of 0 [μs], 0.1 [μs], . . . , 0.8 [μs] of the group G1 are assigned to the transducer a14, a15, . . . , a36 arranged as a 3×3 matrix.

In contrast, in A2 illustrated in FIG. 9, when the delay times are assigned to the arranged transducers a17, a18, a27, a28, a37, a38, a48, a58, a68 arranged in a deformation that is not a 3×3 matrix, for example, the delay times of 0.3 [μs], 0.4 [μs], 0.6 [μs], 0.7 [μs], 0.9 [μs], 1.0 [μs], 1.1 [μs] are assigned to the transducers a17, a18, a27, a28, a37, a38, a48. However, since the delay times to be assigned to the transducers a58 and a68 exceed the range of the delay time of the group (0.3 [μs] to 1.1 [μs]), even if the delay time 1.1 [μs] is assigned to the transducers a58 and a68, the delays of these transducers a58 and a68 become insufficient. The transducers for which delays are insufficient are represented with hatching in FIG. 9.

Thus, a factor in the insufficient delay of the transducer is the fact that the region of the deformation like the region A2 is generated as a fraction if several thousands of transducers are divided into, for example, regions of 3×3 form as in the region A1.

The above problem can be solved by dividing the transducers into regions without fractions; however, even if the region so divided corresponds with, for example, one diagnosis mode, this region does not always correspond with other diagnosis modes. As a result, it is necessary to prepare probes in which divided regions are different in accordance with the diagnosis mode.

For the case in which there is another group with a delay time range exceeding 1.1 [μs], this group is only allowed to correspond with the region A2; however, if the channel of the transducer is forcibly connected to the output terminal of other group by wiring, the wiring is complicated, which is problematic in that it becomes difficult to appropriately assign the delay time of the group to the transducer.

This embodiment is intended to solve the above-described problem, with the object of providing an ultrasound diagnosis apparatus capable of appropriately assigning a delay time of a group to a transducer without complicated wiring.

Means for Solving the Problems

In order to solve the above-described problem, the ultrasound diagnosis apparatus of the embodiment comprises a plurality of transducers, a timing pulse generator, a switch part, and a switch controller. Ultrasound waves are transmitted to the transducers. The timing pulse generator has output terminals for outputting timing pulses based on a delay time to a channel corresponding to each of the transducers, in which a plurality of output terminals are divided into groups and each group has output terminals of a specific number greater than two. The timing pulse generator then generates a transmission delay time within a predetermined time range for the each group. The switch part selectively connects the channels with the output terminals. The switch controller divides the plurality of channels into channel regions of the same number as the specific number and controls the switch part so as to correspond between the groups and the regions by connecting the channels and the output terminals.

BRIEF DESCRIPTION OF THE DRAWINGS

FIG. 2 is a pattern diagram of an ultrasound probe, in which transducers are arranged as a matrix.

FIG. 4 is a pattern diagram illustrating a circuit of a timing pulse generator.

FIG. 5 is a pattern diagram partially illustrating a matrix switch.

MODE FOR CARRYING OUT THE INVENTION

Hereinafter, the ultrasound diagnosis apparatus according to the present embodiment will be described with reference to the drawings.

Figure 1:
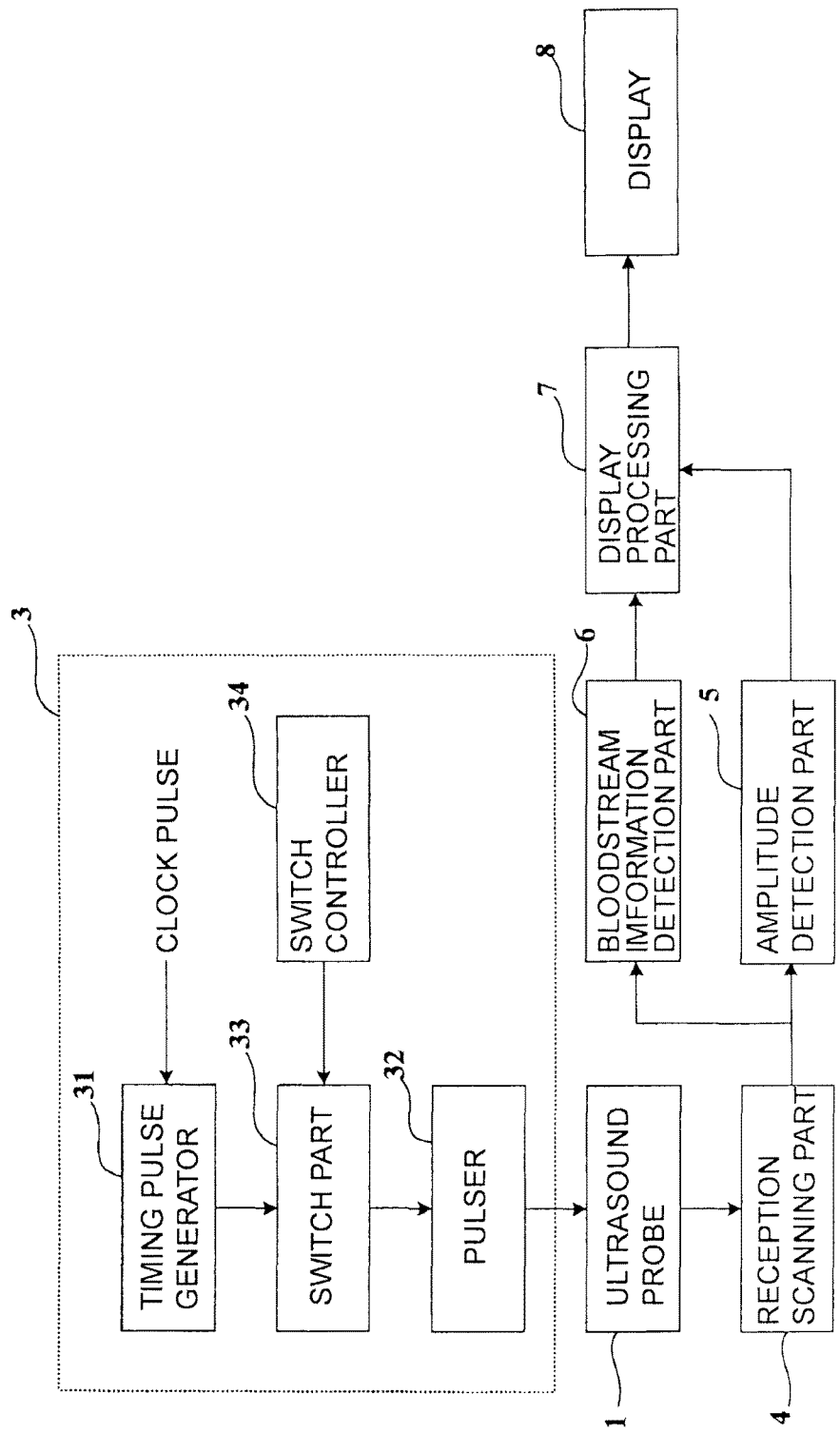
FIG. 1 is a structural block diagram of an ultrasound diagnosis apparatus according to an embodiment.

FIG. 1 is a structural block diagram of an ultrasound diagnosis apparatus according to the embodiment.

As illustrated in FIG. 1, the ultrasound diagnosis apparatus includes an ultrasound probe 1, a transmission circuit 3, a reception scanning part 4, an amplitude detection part 5, a bloodstream information detection part 6, a display processing part 7, and a display 8.

(Ultrasound Probe)

The ultrasound probe 1 has several thousands transducers to mutually convert electric signals and acoustic signals such that the probe 1 can electronically scan the inside of a subject with ultrasound waves at high speed. Respective transducers are arranged as a matrix.

FIG. 2 is a pattern diagram partially illustrating transducers arranged as a matrix.

As illustrated in FIG. 2, for example, the transducers are arranged as a 9×8 matrix. In FIG. 2, the code of the transducer is represented by a combination of number rows and number columns in which the transducer is arranged. For example, the transducers from the first row and the first column to the ninth row and the eighth column are represented by codes from a11 to a98.

Figure 3:
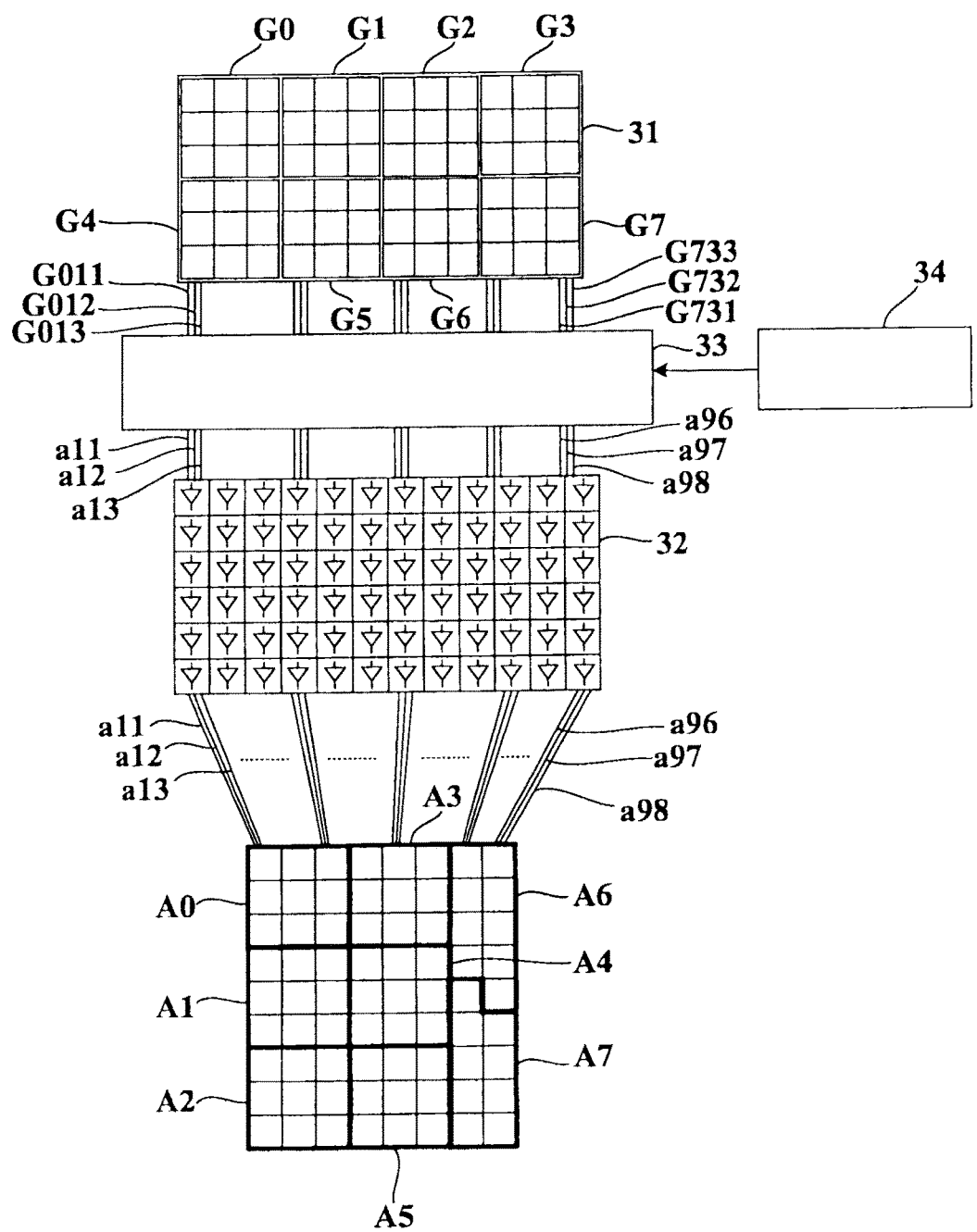
FIG. 3 is a block diagram of a transmission circuit.

FIG. 3 is a block diagram of a transmission circuit. In FIG. 3, channels of the transducers are indicated by codes identical with the codes of the transducers, namely, a11, a12, a13 and a96, a97, a98.

(Transmission Circuit)

Next, the transmission circuit will be described with reference to FIG. 1 and FIG. 3. The transmission circuit 3 includes a clock generator (not shown), a divider (not shown), a timing pulse generator 31, a pulser 32, a switch part 33, and a switch controller 34. The clock generator generates a clock pulse. The divider lowers the clock pulse, for example, to a pulse of about 5 MHz. Further, the ultrasound probe comprises the timing pulse generator 31, the pulser 32, the switch part 33, and the entire or partial switch controller 34. When the switch controller 34 is partially placed on the ultrasound probe, other parts of the switch controller 34 are placed on the main body side of the ultrasound diagnosis apparatus.

The timing pulse generator 31 outputs timing pulses from the output terminal based on this clock pulse. FIG. 3 illustrates a part of the timing pulse generator 31 as a pattern. Next, the timing pulse generator 31 will be described in detail.

The pulser 32 mechanically oscillates the transducer of the ultrasound probe 1 by generating a high-frequency voltage pulse based on the timing pulse and activating the transducer. Thereby, the pulser 32 generates ultrasound waves from the transducer. FIG. 3 illustrates a part of the pulse 32 as a pattern. Next, the pulse 32 will be described in detail.

The generated ultrasound waves are reflected on a boundary of acoustic impedance in the subject before returning to the ultrasound probe 1 and mechanically oscillating the transducer. Thereby, an electric signal is individually generated in each transducer.

(Reception Scanning Part)

The reception scanning part 4 amplifies this electric signal and applies phasing as well as addition to this electric signal. Thereby, a signal having directionality (echo signal) is generated.

(Amplitude Detection Part)

The amplitude detection part 5 generates B mode image data to provide information on the tissue morphology based on the echo signal from the reception scanning part 4. The display processing part 7 displays a sectional image of the tissue morphology using the B mode image data generated by the above-described amplitude detection part 5.

(Bloodstream Information Detection Part)

The bloodstream information detection part 6 is a unit for realizing so-called color Doppler imaging (CDI). The bloodstream information detection part 6 is configured as follows. First, a Doppler signal provided with a frequency shift is derived by detecting the echo signal from the reception scanning part 4 with an orthogonal phase. An operation part then calculates the average rate, dispersion, and power from this frequency by allowing passage of only a specific frequency component from this derived Doppler signal through an MTI filter, and acquiring a frequency of this passed signal by means of an autocorrelator.

Further, by adjusting the pass band of the MTI filter, it is possible to switch modes between a general Doppler mode (the image data according to this mode is referred to as bloodstream Doppler image data) that mainly images the bloodstream and a tissue Doppler mode (the image data according to this mode is referred to as tissue Doppler image data) that mainly images organs such as the myocardium.

(Display Processing Part, Display)

In addition, the display processing part 7 composes the bloodstream Doppler image data and the tissue morphology image data generated by the above-described bloodstream information detection part 6, and displays the composition image thereof. The composition image of the tissue morphology image data and the functional image data is displayed on the display 8.

Subsequently, the details of the transmission circuit 3 will be described with reference to FIG. 3 and FIG. 4. FIG. 4 is a pattern diagram illustrating a circuit of the timing pulse generator 31.

(Timing Pulse Generator)

The timing pulse generator 31 is divided into a plurality (for example, 200 to 300) of groups. In FIG. 3, the extracted 8 groups are depicted by the codes G0 to G7.

Figure 8:
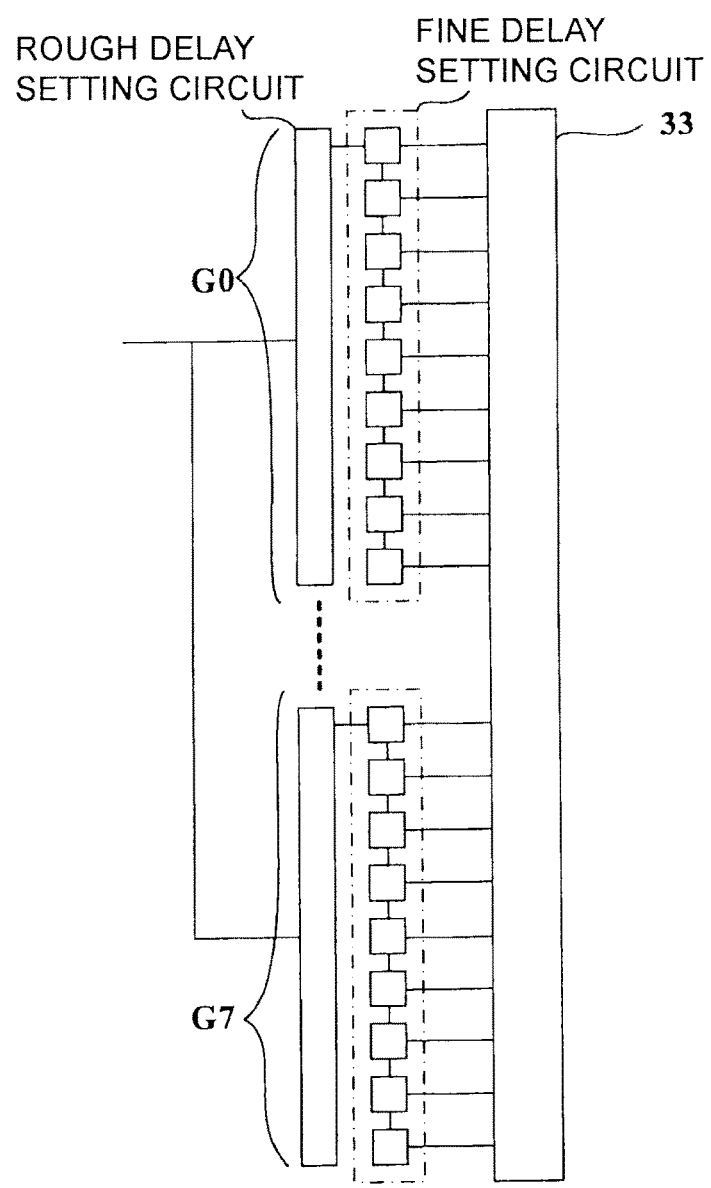
FIG. 8 is a pattern diagram illustrating a circuit structure of a group.

Respective groups comprise the same structures. Hereinafter, a representative group will be described. This group is made up of one circuit for setting the time from 0 [µs] to 7 [µS] for each rough delay time (for example, 1.0 µS) (a rough delay setting circuit: refer to FIG. 8), and nine circuits for setting the time from 0 [µs] to 0.8 [µs] for each fine delay time (for example, 0.1 [µs]) (a fine delay setting circuit).

The delay time set by the group is composed by the addition of the rough delay time and the fine delay time. For example, in the group G0, when the rough delay time is 5.0 [µs], and the fine delay times are 0 [µs], 0.1 [µs], . . . , 0.8 [µs], the delay time of the group G0 is 5.0 [µs], 5.1 [µs], . . . , 5.8 [µs].

In addition, for example, in the group G1, when the rough delay time is 6.0 [µs], and the fine delay times are 0 [µs], 0.1 [µs], . . . , 0.8 [µs], the delay time of the group G0 is 6.0 [µs], 6.1 [µs], . . . , 6.8 [µs].

As described above, by making the rough delay time to be combined with the fine delay time different between the groups, it is possible to provide various types of transmission delay times to be assigned to the transducers.

In FIG. 4, the fine delay setting circuits arranged as a 3×3 matrix are represented as a combination of group codes, along with number rows and number columns. For example, in the group G0, the fine delay setting circuits placed on the first row, first column to third row, and third column are represented by the codes G011 to G033. In addition, for example, in the group G7, the fine delay setting circuits placed on the first row, first column to third row, and third column are represented by the codes G711 to G733.

Further, the output terminal of the fine delay setting circuit is illustrated in FIG. 3 along with the same code as that of the circuit. In FIG. 3, as a representative, the output terminals of the fine delay setting circuits G011, G012, and G013 in the group G0 are represented by the codes of G011, G012, and G013. In addition, the output terminals of the fine delay setting circuits G731, G732, and G733 in the group G7 are represented by the codes of G731, G732, and G733. For example, timing pulses to be output from the output terminals of G011 to G033 are provided with delay times of 5.0 [µs], 5.1 [µs], . . . 5.8 [µs].

(Pulser)

Next, the pulser 32 will be described with reference to FIG. 3. FIG. 3 illustrates a pulser 32 in which a plurality of amplifiers making up the pulser 32 are arranged as a matrix. The pulser 32 is arranged between the switch part 33 and the ultrasound probe 1, the input terminals of the amplifiers are connected to the output terminals of the timing pulse generator 31 via the switch part 33, and the output sides of the amplifiers are connected to the channels of the transducers. FIG. 3 illustrates the input terminals of the amplifiers provided with the same codes a11, a12, a13, a96, a97, and a98 as the codes of the channels to which the output terminals of these amplifiers are connected.

(Switch Part)

Subsequently, the switch part 33 including the matrix switch will be described with reference to FIG. 3 to FIG. 6. In FIG. 3, the matrix switch is represented by an imaginary line. As an example of the matrix switch, a MEMS (Micro Electro Mechanical Systems) switch is used which is a device having parts composing the switch accumulated on a substrate made of silicon or glass.

The matrix switch selectively connects the output terminals of the timing pulse generator 31 to the channels in accordance with instructions from the switch controller 34.

In the matrix switch, a plurality of signal lines on the input side and a plurality of signal lines on the output side are arranged according to a grid system, with open-close switches arranged at positions such that the signal lines intersect each other.

As illustrated in FIG. 3, the signal lines on the input side are connected to respective output terminals G011 to G731 of the groups G0 to G7, while the signal lines on the output side are connected to respective channels a11 to a98 of the transducers. The timing pulses input from the output terminals are distributed to respective channels in accordance with ON and OFF of the open-close switches.

Figure 6:
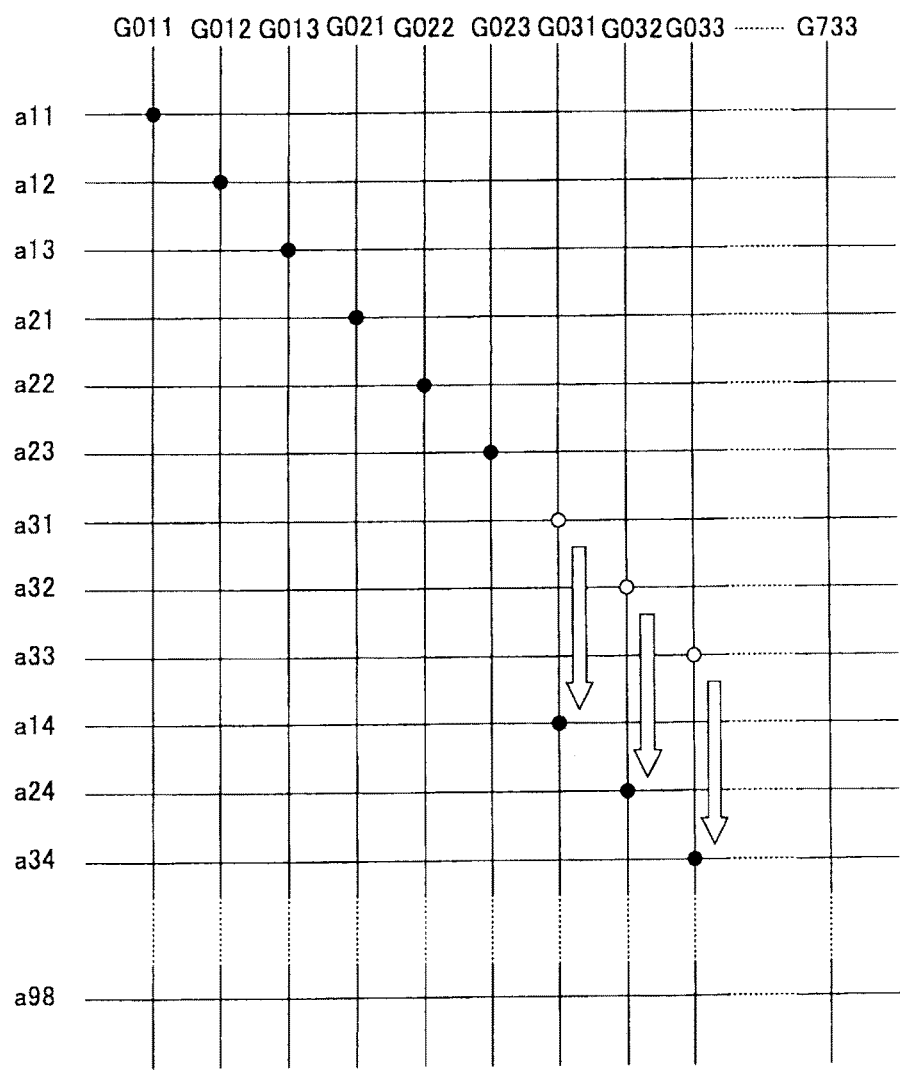
FIG. 6 is a pattern diagram partially illustrating the matrix switch.

FIG. 5 is a pattern diagram partially illustrating the matrix switch. In FIG. 5, the output terminals of the group G0 are represented by the codes G011 to G033, the channels from first row, first column to third row, third column by a11 to a33, and further, represents the channels from first row, fourth column, second row, forth column, and third row, fourth column by a14, a24, and a34. Further, turning on of the open-close switches is illustrated in FIG. 6 by a black circle.

In the state of the open-close switches illustrated in FIG. 5, the timing pulses output from the output terminals G011 to G033 of the group G0 are distributed to the channels a11 to a33. The transducers corresponding to the channels a11 to a33 to which the timing pulses of the group G0 are distributed are illustrated in FIG. 2 by the region A0 encircled by a bold line.

As described above, by controlling the open-close switches, it is possible to correspond between the group G0 and the region A0 and the timing pulses of the group G0 can be distributed to the transducers in the region A0.

In the same way, by controlling the open-close switches, it is possible to correspond between other groups and regions.

FIG. 6 is a pattern diagram partially illustrating the matrix switch. In FIG. 6, the open-close switches turned off from on are represented by white circles, and the open-close switches turned on from off are represented by black circles.

Figure 7:
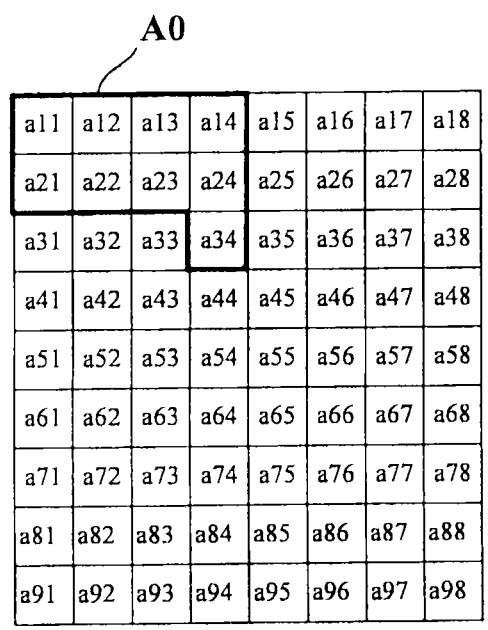
FIG. 7 is a pattern diagram partially illustrating the ultrasound probe.

In the state of the open-close switches illustrated in FIG. 6, the timing pulses output from the output terminals G011 to G033 of the group G0 are distributed to the channels a11 to a14, a21 to a24, and a34. The transducer regions corresponding to the channels a11 to a14, a21 to a24, and a34 to which the timing pulses of the group G0 are distributed are illustrated in FIG. 7 by the region A0 encircled by a bold line.

In the region A0 illustrated in FIG. 7, any transducer in the region A0 meets selected conditions (to be described later), and is located within a delay time range that can set a group (for example, 0 [μs] to 0.8 [μs]).

For example, the delay times 0 [μs], 0.1 [μs], 0.2 [μs], 0.3 [μs], 0.4 [μs], 0.5 [μs], 0.6 [μs], 0.7 [μs], and 0.8 [μs] are assigned to the transducers a11, a12, a13, a14, a21, a22, a23, a24, and a34 within the region A0.

As described above, by controlling the open-close switches, it is possible to correspond between the group G0 and a new region A0, subsequently, the timing pulses of the group G0 can be distributed to the transducers in the new region A0.

In the same way, by controlling the open-close switches, it is possible to correspond between other groups and new regions.

(Switch Controller)

Next, the switch controller 34 will be described with reference to FIG. 1, FIG. 2, and FIG. 7.

The switch controller 34 controls the open-close switches to select the region corresponding to the group. Further, the switch controller 34 selects the region corresponding to the group by a circulatory organ diagnosis every time transmission and reception of all transducers are terminated, and in the abdomen and by general diagnosis every time transmission and reception of the transducers of the set group are terminated.

As a condition for selecting the region, it is considered that, in the region, the transducers are arranged adjacent to each other and no transducer is separated from the other transducers by more than a specific number thereof.

Next, the conditions for selecting the region (selecting conditions) will be described.

The selecting conditions are stored in storage (not shown) as a combination pattern of the outline forms of the regions. The pattern corresponds to identification information of the ultrasound probe and the diagnosis mode. The storage is provided in the ultrasound probe or the main body of the ultrasound diagnosis apparatus.

The outline form of the region includes a 3×3 form (the form in which the transducers are arranged as a 3×3 matrix), and its deformation (including the form in which the transducers are arranged as a 1×9 matrix.)

Whether or not the pattern meets the selecting conditions depends on the delay circuit performance and physical form (measurement) of the transducer, and from experience, it can be said that there are two selecting conditions. One condition is that nine transducers in a region be arranged adjacent to each other while the other condition is that no transducer be separated from the other transducers by more than the specific number thereof in the region. Here, when the transducers are separated from each other by more than the specific number thereof, defining the specific number as M, if the number of transducers is increased in accordance with separation by one transducer such that any transducer is defined as "0," the transducer that is separated from "0" by one transducer in a row direction or a column direction is defined as "1," while the transducer that is further separated from "1" by one transducer in a row direction or a column direction is defined as "2," the transducer defined as "M" becomes a transducer separated from "0" by M transducers.

Figure 9:
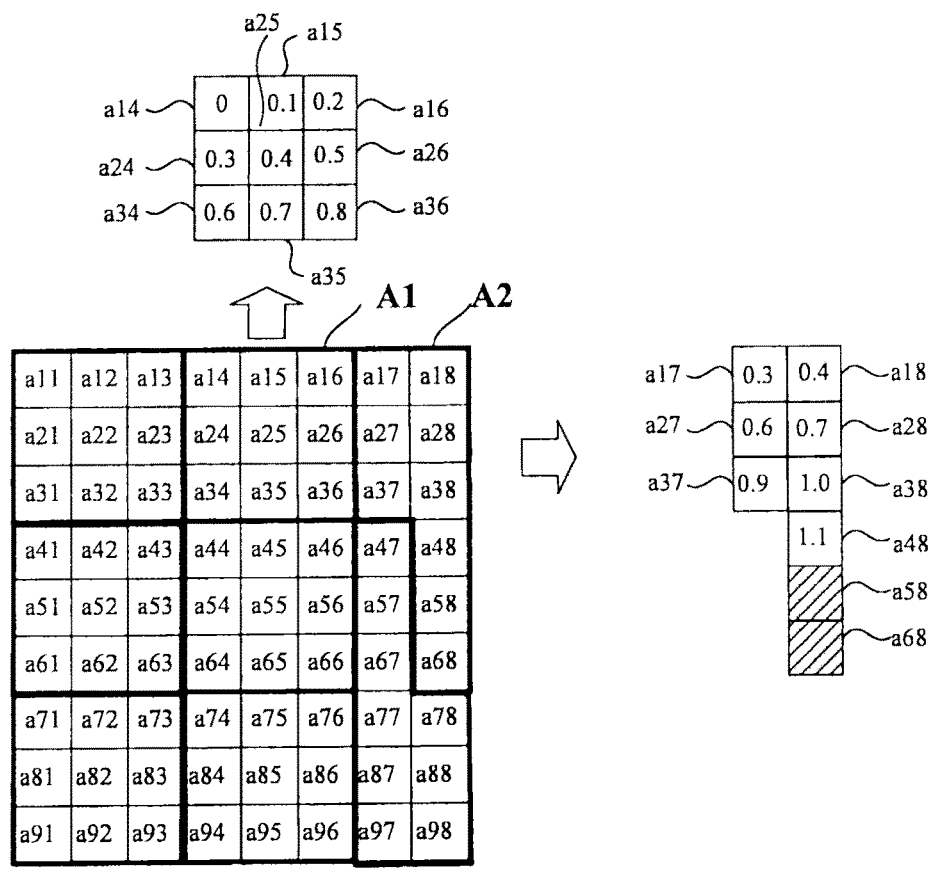
FIG. 9 is a pattern diagram partially illustrating an ultrasound probe according to a comparative example.

An example of the pattern that does not meet the selecting conditions includes a deformation as with the region A2 illustrated in FIG. 9. This deformed region A2 includes transducers arranged separated by more than 4 transducers. In other words, if a17 is defined as "0," a58 is "5," and a68 is "6." In this case, respective transducers a58 and a68 are arranged separated from "0" by greater than 4 transducers. Here, the transducer a17 to which the earliest delay time is assigned is defined as "0."

Figure 10:
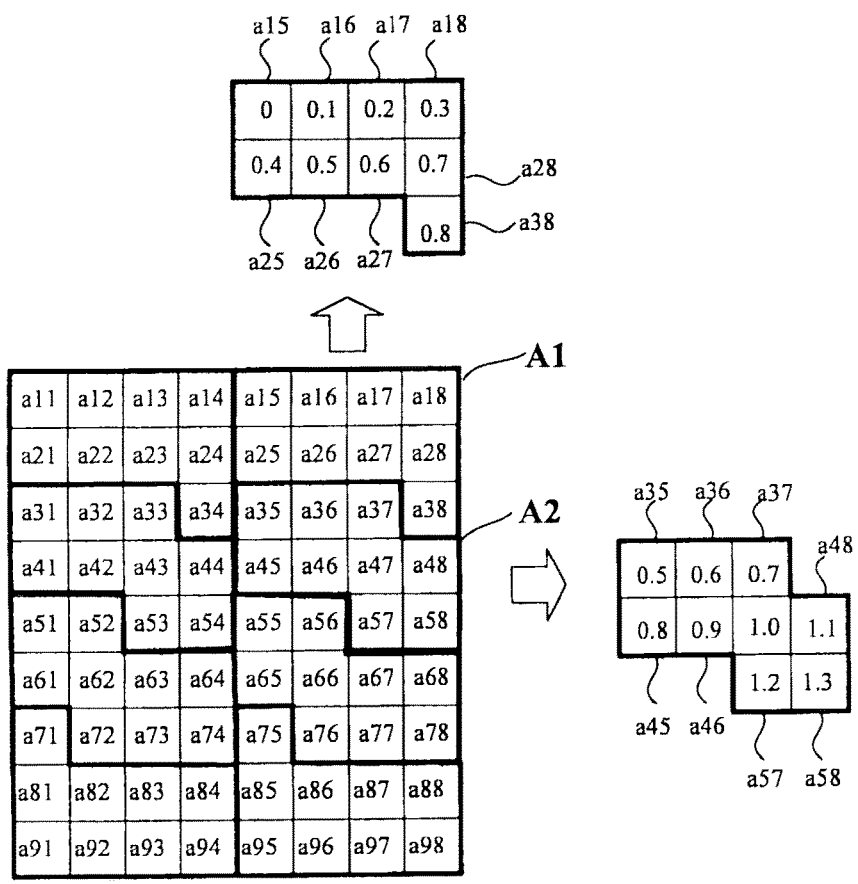
FIG. 10 is a pattern diagram partially illustrating the ultrasound probe according to the comparative example.

FIG. 10 is a pattern diagram partially illustrating the ultrasound probe according to a comparative example.

An example of the pattern that meets the selecting conditions includes a combination pattern of the deformations illustrated in FIG. 10.

The region A1 illustrated in FIG. 10 does not include a transducer separated from "0" by greater than 5 transducers. In other words, if a15 is defined as "0," a16 and a25 are "1," a17 and a26 are "2," a18 and a27 are "3," a28 is "4," and a38 is "5," so that no transducer is arranged separated from "0" by greater than 5 transducers. Here, the transducer a15 to which the earliest delay time is assigned is defined as "0."

In addition, the region A2 also includes no transducer separated from "0" by greater than 5 transducers. In other words, if a35 is defined as "0," a36 and a45 are "1," a37 and a46 are "2," a47 is "3," a48 and a57 are "4," and a58 is "5," so that no transducer is arranged separated from "0" by greater than 5 transducers. Here, the transducer a35 to which the earliest delay time is assigned is defined as "0."

The switch controller 34 selects the region to be allowed to correspond to the group from the storage based on the identification information of the ultrasound probe and the diagnosis mode. The switch controller 34 may select a region that meets the selecting conditions while obtaining a candidate of the region to be allowed to correspond to the group and calculating if this candidate meets the selecting conditions.

Next, it will be described if sufficient delay times are assigned to respective transducers in the regions A1 and A2 illustrated in FIG. 10. The ranges of the delay times of the groups G1 and G2 are defined as 0 [μs] to 0.8 [μs] and 0.5 [μs] to 1.3 [μs].

The delay times of 0 [μs], 0.1 [μs], 0.2 [μs], 0.3 [μs], 0.4 [μs], 0.5 [μs], 0.6 [μs], 0.7 [μs], and 0.8 [μs] are assigned to the transducers a14, a15, a16, a24, a25, a26, a34, a35, and a36 in the region A1. In other words, it is possible to appropriately assign the delay time of the group G1 to the transducer in the region A1.

In addition, the delay times of 0.5 [μs], 0.6 [μs], 0.7 [μs], 0.8 [μs], 0.9 [μs], 1.0 [μs], 1.1 [μs], 1.2 [μs], and 1.3 [μs] are assigned to the transducers a35, a36, a37, a45, a46, a47, a48, a57, and a58 in the region A2. In other words, it is possible to appropriately assign the delay time of the group G2 to the transducer in the region A2.

(Operation)

Figure 11:
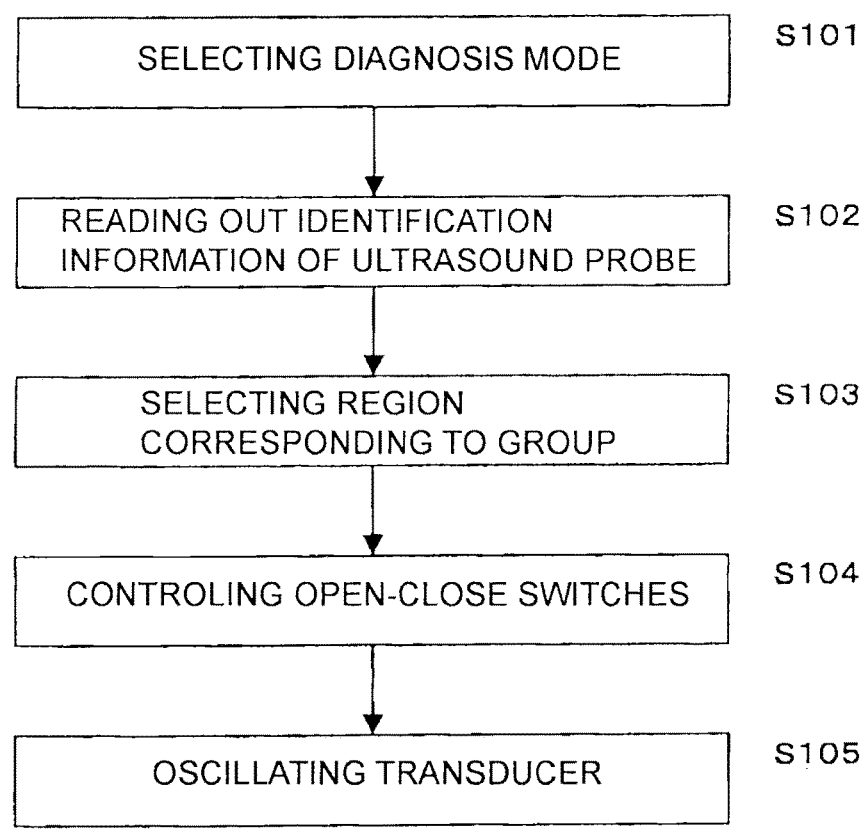
FIG. 11 is a flowchart illustrating the operation from the selection of a diagnosis mode until the transmission of ultrasound waves.

Next, the operation of the transmission circuit 3 will be described with reference to FIG. 11. FIG. 11 is a flowchart illustrating the operation from selection of the diagnosis mode until the transmission of ultrasound waves.

(S101)

As illustrated in FIG. 11, first, the diagnosis mode is selected. The diagnosis mode is input by an input part in the main body of the ultrasound diagnosis apparatus, and stored in the storage (not shown) of the body. The input diagnosis mode is read from the storage by the switch controller 34. Examples of the diagnosis mode include an A mode, a B mode, an M mode, a Doppler mode, a color Doppler mode, a 4D mode, and a diagnosis object (a circular organ, an abdomen, and the like) The 4D mode serves to reconstruct real time 3D images.

(S102)

Then, the identification information of the ultrasound probe is read out. The identification information is stored in the storage (not shown) of the ultrasound probe. Connecting the ultrasound probe to the body of the ultrasound diagnosis apparatus, the identification information is read out from the storage by the switch controller 34.

(S103)

Subsequently, the switch controller 34 selects the region corresponding to the group from the storage based on the diagnosis mode and the identification information of the ultrasound probe.

(S104)

Then, the switch controller 34 controls the open-close switches so as to correspond between the groups and the regions.

(S105)

Subsequently, the timing pulse generator 31 outputs the timing pulses from the output terminals of respective groups to respective channels. The pulser 32 generates a high-frequency voltage pulse based on the timing pulses, and mechanically oscillates the transducer. Thereby, the ultrasound waves are transmitted from the transducer.

In this embodiment, the switch controller 34 controls the switch part 33 so as to select the region of the transducer allowed to correspond to the group, thereby making it possible to appropriately assign the delay time of the group to the transducer without complicated wiring.

In the embodiment, by combining the rough delay setting circuit to nine fine delay setting circuits, the groups of the timing pulse generator 31 are constructed. However, this combination has been limited to the combination between the fine delay setting circuits and the rough delay setting circuit in one group.

In contrast, by providing the switch part between the fine delay setting circuits in one group and the rough delay setting circuit of another group, the fine delay setting circuits in one group are combined with the rough delay setting circuit of the other group. Thereby, the settable delay time range is increased, and as a result, the circuit size can be further decreased. Further, if the transmission circuit is constructed so as to have a plurality of transmission waveform generation circuits and selects these circuits by the switch part, it is possible to transmit the waveforms with a plurality of frequencies.

Some embodiments according to the present invention have been described above; however, these embodiments are presented as examples and are not intended to limit the range of the invention. These novel embodiments may be implemented in other various forms, and various omissions, replacement, and changes may be made without departing from the scope of the invention. These embodiments and variations thereof are included in the range and scope of the invention, as well as included in the invention set forth in Claims the range of the equivalents thereof.

EXPLANATION OF SYMBOLS

1 ultrasound probe
3 transmission circuit
31 timing pulse generator
32 pulser
33 switch part
34 switch controller
4 reception scanning part
5 amplitude detection part
6 bloodstream information detection part
7 display processing part
8 display

The invention claimed is:

1. An ultrasound diagnosis apparatus comprising:
   a two-dimensional array of a plurality of transducers from which ultrasound waves are transmitted;
   an ultrasound probe including the transducers with identification information for the transducers;
   a timing pulse generator having output terminals for outputting timing pulses based on a transmission delay time to channels corresponding to respective of the transducers, in which the plurality of output terminals are divided into groups, with each group having the output terminals of a specific number greater than two, and the timing pulse generator being configured to generate the transmission delay time within a predetermined time range for the each group;
   a switch part configured to selectively connect the channels with the output terminals, and
   a switch controller configured to divide the plurality of channels into channel regions of the same number as the specific number of output terminals based on the identification information, cause the channels to be connected with the output terminals and control the switch part so that there is connection correspondence between the groups and the channel regions,
   wherein the switch controller is configured to divide the plurality of channels corresponding to respective transducers into the channel regions, including channel regions in which the transducers are arranged in a two-dimensional array, so that, for each channel region, the respective transducers corresponding to each channel region have a transducer arrangement in which each transducer within the transducer arrangement is adjacent to another transducer within said transducer arrangement and is separated from each other transducer within said transducer arrangement by no more than a specific number of transducers within said transducer arrangement.

2. The ultrasound diagnosis apparatus according to claim 1, wherein the switch controller is configured to divide the transducers at the timing when the ultrasound waves are transmitted and received.

3. The ultrasound diagnosis apparatus according to claim 1, wherein the ultrasound probe is used correspondingly to a diagnosis mode, and the switch controller is configured to divide the transducers correspondingly to the diagnosis mode based on the identification information of the ultrasound probe.

* * * * *